US006363393B1

(12) United States Patent
Ribitzky

(10) Patent No.: US 6,363,393 B1
(45) Date of Patent: Mar. 26, 2002

(54) COMPONENT BASED OBJECT-RELATIONAL DATABASE INFRASTRUCTURE AND USER INTERFACE

(76) Inventor: Ron Ribitzky, 46 Beverly Rd., Atlanta, GA (US) 30309

( * ) Notice: Subject to any disclaimer, the term of this patent is extended or adjusted under 35 U.S.C. 154(b) by 0 days.

(21) Appl. No.: 09/255,547

(22) Filed: Feb. 22, 1999

Related U.S. Application Data

(60) Provisional application No. 60/075,570, filed on Feb. 23, 1998.

(51) Int. Cl.[7] ............................................. G06F 17/30
(52) U.S. Cl. ............................ 707/102; 707/2; 707/3; 707/4; 707/10; 707/103 Y; 707/103; 709/201; 709/203; 705/1; 705/2; 705/3; 345/762; 345/763; 345/781; 345/967; 345/968
(58) Field of Search ............................... 707/2, 3, 4, 10, 707/103, 102, 103 Y; 705/1–3, 4; 345/340, 348, 349, 762, 763, 781, 967, 968; 709/201, 203

(56) References Cited

U.S. PATENT DOCUMENTS

| | | | | |
|---|---|---|---|---|
| 5,428,734 A | | 6/1995 | Haynes et al. ............... 345/769 |
| 5,546,527 A | | 8/1996 | Fitzpatrick et al. .......... 345/769 |
| 5,611,031 A | | 3/1997 | Hertzfield et al. ............ 345/740 |
| 5,630,080 A | | 5/1997 | Malamud et al. ............ 345/769 |
| 5,652,842 A | | 7/1997 | Siegrist, Jr. et al. ............. 705/2 |
| 5,664,109 A | * | 9/1997 | Johnson et al. ................. 705/2 |
| 5,715,413 A | * | 2/1998 | Ishai et al. .................... 345/349 |
| 5,732,230 A | | 3/1998 | Cullen et al. ................ 345/764 |
| 5,970,475 A | * | 10/1999 | Barnes et al. .................. 705/27 |
| 6,018,713 A | * | 1/2000 | Coli et al. ....................... 705/2 |
| 6,067,523 A | * | 5/2000 | Bair et al. ....................... 705/3 |
| 6,073,105 A | * | 6/2000 | Sutcliffe et al. ................ 705/1 |
| 6,112,183 A | * | 8/2000 | Swanson et al. ................ 705/2 |
| 6,151,581 A | * | 11/2000 | Kraftson et al. ................ 705/3 |
| 6,151,586 A | * | 11/2000 | Brown .......................... 705/14 |
| 6,154,729 A | * | 11/2000 | Cannon et al. ................ 705/35 |

FOREIGN PATENT DOCUMENTS

| | | | |
|---|---|---|---|
| EP | 0592046 | 10/1993 | ........... G06F/15/40 |
| WO | 9102304 | 2/1991 | ........... G06F/3/023 |
| WO | 9208184 | 5/1992 | ............. G06F/3/14 |

* cited by examiner

Primary Examiner—Jack Choules
Assistant Examiner—Cheryl Lewis
(74) Attorney, Agent, or Firm—Nutter McClennen & Fish LLP

(57) ABSTRACT

The invention provides a system for accessing business data stored in one or more databases by a user. The system includes a means for presenting a user with a plurality of components with each component representing a discrete element of the business model, having a defined relationship with each other component, and including a plurality of information objects. Each information object represents an instance of the component business element and can be defined by a set of attributes and behaviors. The system further provides means for user selection of a first one of the plurality of components, for user selection of a first one of the plurality of information objects from the first component, and for instantiating the first information object. The user can then manipulate the first information object to cause the object to interact with any of the other components. The system then generates a report showing information objects of the other component which represent instances of the other component that are related to the first information object.

17 Claims, 13 Drawing Sheets

Select

Client | Group | Views

First name: jo
Nickname: Joanie / Joann / Joanna / Joanne

Last name:

☐ Female  ☐ Male

Age:
Born: Month / Year
Client ID:

5616 out of 5616 match the criteria

☑ Confidential Medical Information

[OK]   View Result   [Cancel]

Encounter profile for client Jose Givens on 04/22/1996

905

Client
- Jose Givens
- Age on Encounter: 1 6/12    Gender: Male

Provider
- Laveda M Doxey
- Barbara M Weissman
- Bruce Keisling
- Susan J Coniglio
- Elizabeth Weil Monday
Apr 22/1996

Service
- Detailed Consult (40 Min)

Problems
1: Development Delays
2: Seizure Disorder
3:
4:

Reports and Views
- ☐ Client Encounter Form-Summary
- ☐ Client Encounter Form-Detail
- ☐ Devel. Pediatric Initial Evaluation
- ☐ Devel. Pediatric Followup
- ☐ Phone Encounter
- ☐ Confidential Psychological Evaluation
- ☐ Family Social History Assessment
- ☐ Team Interdisciplinary Evaluation
- ☐ Team Interdisciplinary Followup
- ☐ Therapy Evaluation
- ☐ Therapy Progress Note
- ☐ Devel. Need Screening Assessment ☐ Confidential Medical Information

[OK]    [Cancel]

*Figure 9A*

COMPONENT BASED OBJECT-RELATIONAL DATABASE INFRASTRUCTURE AND USER INTERFACE

CROSS REFERENCE TO RELATED APPLICATION

This application claims the benefit of U.S. Provisional Application 60/075,570, filed on Feb. 23, 1998, and specifically incorporates the contents of that application herein by reference.

STATEMENT REGARDING FEDERALLY SPONSORED RESEARCH

Not applicable.

1. A Field of the Invention

The invention provides a method, and architecture for providing a component based object-relational database infrastructure and a visual interface for presenting data, information, documents, and knowledge that are managed by or through that database to a user.

2. Background of the Invention

Due to a variety of economic, regulatory, and care related influences, healthcare organizations need to invest in information technology that supports the interdisciplinary and cross-departmental process of care of an individual patient throughout a number of encounters over a long period of time and, very often, across multiple geographic locations. The key trends driving this investment need include the massive transition to managed-care, the growing share of capitated contracts in the healthcare revenue structure, the emergence of disease-management practices, and accreditation requirements for outcome reporting. The common denominator in these trends is the recognition that the patient is a client of the entire organization rather than a client of distinct departments or service providers.

Users of healthcare information technology systems are also pressing for new and improved information capabilities that will allow them to readily access stored knowledge that centers around a patient, a patient's problems, and the services provided to a patient. In addition, administrators and analysts need to access data that will allow them to identify and adopt "best practices" across a healthcare organization to improve patient service while reducing or limiting cost.

Existing healthcare information technology fails to meet the needs of the industry. To date, the primary focus of healthcare information systems has been primarily to automate the administrative and financial functions of discrete departments. This focus has left many healthcare organizations with incompatible legacy systems that do not allow them to access their stored information in a way that their business now requires.

New technology has been applied to healthcare and other information systems in an attempt to provide the type of access to enterprise wide information that many businesses require. Object-oriented programming techniques and databases have been applied to this problem and object-oriented technology is making great strides among technologists. The benefit of this technology has not yet trickled down to the end users. User interfaces to object-oriented systems and databases are typically standard windows based graphical user interfaces, which even after great effort to tailor the graphical user interface (GUI) to a particular business need, require extensive training for end users and provide access to the stored information in very limited ways. In addition, data from these database systems is typically accessed and provided in a tabular format that requires much study to decipher or use.

Another technology applied to this problem is data warehousing. A data warehouse is a computer system that collects and analyzes summary data from different business units in an organization on a periodical basis. Data in the data warehouse is typically supplied from data marts which are smaller scale databases that are tailored to contain only information from a particular business unit or subset of the enterprise. The data warehouse includes information about how the warehouse is organized and any connections between data. Generally, this allows a user of the data warehouse to access data through what appears to be a single server to analyze trends in the overall business. OLAP (on-line analytical processing) databases are sometimes used with data warehouses. OLAP databases are relational database systems capable of handling queries that are more complex than standard relational databases through multi-dimensional access to data and special indexing techniques.

While data warehousing is useful for some purposes, it is of little help to a healthcare professional trying to provide service to a patient who needs instantaneous access to each problem reported by this patient in each of the patient's encounters with the healthcare organization. In addition, user interfaces to data warehouses are typically standard windows GUIs and the data is accessed by and provided to the end user in tabular format.

The clinical data repository is another approach to curing the ills of healthcare information technology. A clinical data repository is a computer system that collects and analyzes data from different clinical information systems in the organization. Clinical information systems include Orders, Labs, Pharmacy, Radiology, and other systems that capture and process clinical data. As with the other systems described, clinical data repositories are limited in the scope of the data that they serve by virtue of being designed for clinical data while related financial and management data is typically managed by separate data warehouses.

Information technology should provide clinicians and management with activity and financial information for operational effectiveness, quality of care, economic viability, and competitive strategy development. Despite these clearly defined needs, clinicians and management remain handicapped by the lack of timely patient history and encounter data that is fragmented across dozens of different legacy systems. There is no transaction system in place today that is capable of generating integrated views of the key elements that drive the healthcare business. The healthcare business is not unique in this regard, a database or transaction system that meets the needs of the healthcare industry could benefit many other businesses that are struggling with similar problems.

SUMMARY OF THE INVENTION

The present invention meets the aforementioned needs by providing a component based object-relational database infrastructure and user interface. The database infrastructure (DBI) of the invention uses object oriented techniques to describe a business model that is implemented using object-oriented software technology. The user uses or interacts with the database though a component based, object-oriented user interface that presents discrete business model components to the user for manipulation. In particular, the business model is composed of a discrete set of inter-related components where each component is a key element in the business and includes certain attributes and behaviors.

In the system of the invention, a user selects one component of the business model, instantiates an object of that component, then manipulates the object to cause it to interact with another component to generate one or more reports showing information objects and data that explain the relationship between the object and the component it interacts with. The user may then instantiate further objects or examine further relationships.

In one embodiment, the invention provides a system for accessing business data stored in one or more databases by a user. The system presents the user with a plurality of components where each component represents a discrete element of the business model, has a defined relationship with each other component, and includes any number of information objects. Each information object represents an instance of the component business element and can be defined by a particular set of attributes and behaviors. The system further provides means for user selection of a first one of the components, user selection of a first one of the information objects from the first component, and instantiating the first information object. The user can then manipulate the first information object to cause the object to interact with any of the other components. The system then generates a report showing information objects of the other component which represent instances of the other component that are related to the first information object.

In the context of a healthcare business, one component in the business model could be a "client" of the healthcare business. Individual patients can then be represented as instances of the client component having particular values for the attributes defined by the component. In the system of the invention, a user selects one component of the business model (such as the client component), instantiates an object of that component (such as a particular patient), then manipulates the object to cause it to interact with another component to generate one or more reports showing information objects and data that explain the relationship between the object and the component it interacts with. For example, the user could cause the patent object to interact with a "providers" component to generate a report of each doctor or nurse that the patient has been seen by. The user may then instantiate further objects or examine further relationships.

In another embodiment, the invention provides a database infrastructure for implementing a relational data model that supports an object oriented business model having a plurality of components with each component representing a discrete element of a business model. The infrastructure includes a relational data server, an object relational server, and a user interface server. The relational data server processes relational database requests. The object relational server includes a plurality of component servers with each component server corresponding to one of the discrete components of the object oriented business model. The object relational server communicates with the relational data server to provide data, information, and knowledge services for its respective components. The user interface server displays the components of the object oriented business model and other components to a user and supports user manipulation of those components in a user-centric visual fashion.

The database infrastructure may further include a security server for authenticating users who attempt to log in to the system, a document server for serving documents such as spreadsheet or word-processing documents to the component servers, and a gateway server for linking the database infrastructure to external software applications having source data for the databases.

The invention also provides a business model that is specific to the healthcare industry. In particular, a healthcare enterprise is modeled as having discrete client, problem, provider, service and encounter components. These components inter-relate in that a client who comes to the enterprise typically comes because that client has a problem. The client having a problem then has an encounter with a provider who performs a service for the client. In accordance with the invention, this model is implemented using object-oriented techniques and a user-centric visual interface to allow a user of the system to rapidly and easily access any information in the enterprise's Data-Base Infrastructure according to the relationships between the model components.

The database infrastructure and user-centric visual interface of the invention can be applied to variety of industries in addition to the healthcare industry. Any business that can be modeled with a number of core components having defined or definable inter-relationships can employ the system of the invention to present those core components to a user in an object-oriented manner to provide the benefits described herein. Once the industry specific business model components are finalized, an existing database infrastructure can be reused by adapting it to the new components to rapidly develop a new software system for the new business model.

BRIEF DESCRIPTION OF THE DRAWINGS

The features of the invention may be more fully understood from the following detailed description of the drawings in which:

FIG. 5A illustrates a data selection screen useful for implementing the process flow of FIG. 5.

FIG. 6A illustrates a profile display indicating the attributes of a particular client selected by a user.

FIG. 9A illustrates a page report screen useful for detailed reporting on an encounter selected as in FIGS. 9 and 10.

DETAILED DESCRIPTION OF THE INVENTION

Figure 1:
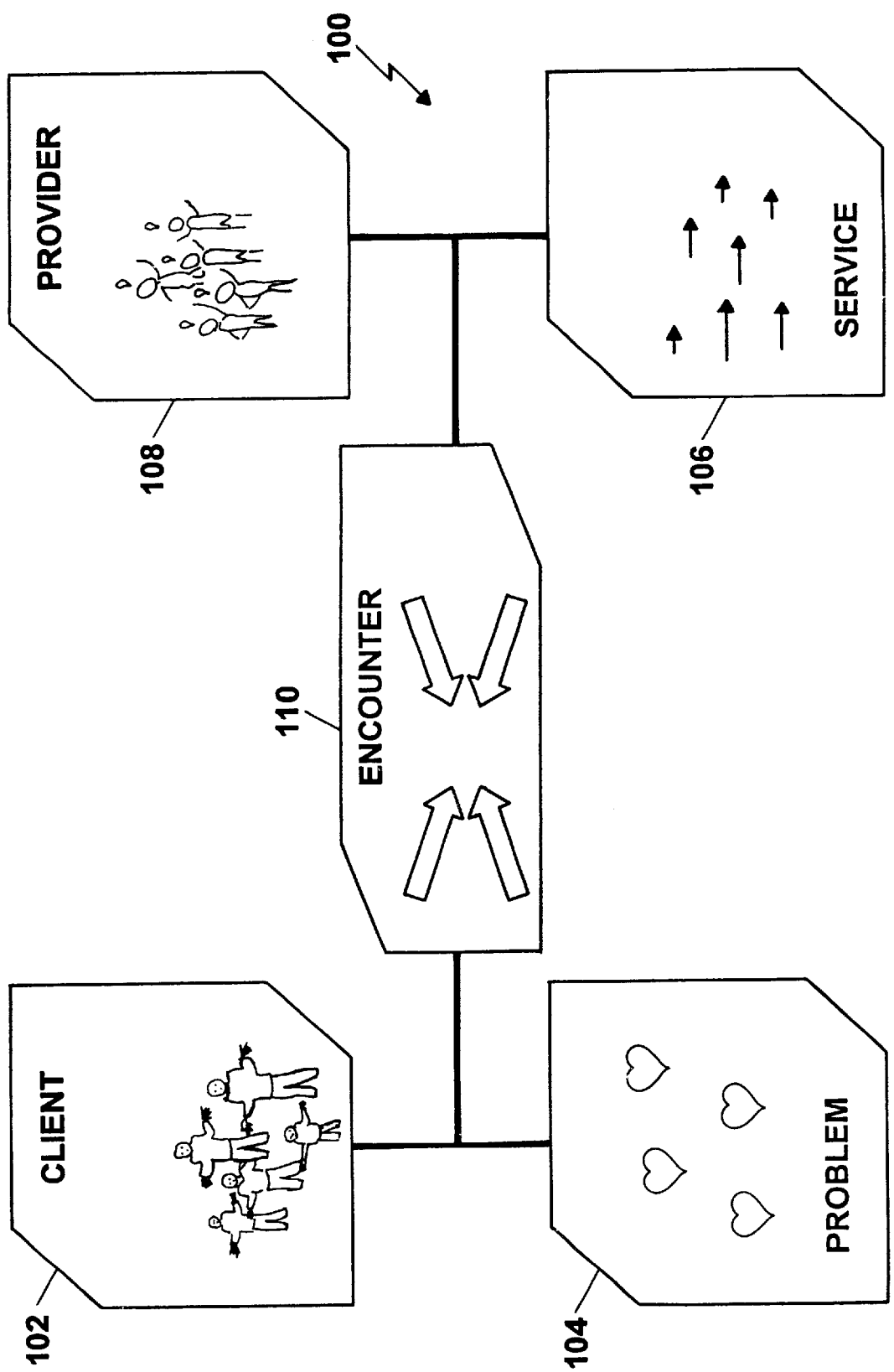
FIG. 1 is a graphical representation of a healthcare business model of the invention.

The present invention provides a component based object-oriented database infrastructure and user visual interface. The database infrastructure (DBI) of the invention uses object oriented techniques to describe a business model that is implemented using object-oriented software technology to present the business model to a user. The user uses or interacts with the database though a component based, object-oriented user interface.

In particular, the business model is composed of a discrete set of inter-related components. Each component is a key element in the business and includes certain attributes and behaviors. Each component can be instantiated into a series of objects, each object representing an instance of that component and having the attributes and behaviors that are defined by the component. For example, one component in the healthcare industry could be a "client" of the healthcare enterprise. Individual patients can then be represented as instances of the client component having particular values for the attributes defined by the component. In the system of the invention, a user selects one component of the business model, instantiates an object of that component, then manipulates the object to cause it to interact with another component to generate one or more reports showing information objects and data that explain the relationship between the object and the component it interacts with. The user may then instantiate further objects or examine further relationships. This system can conveniently be developed using object-oriented computer programming techniques.

Object-oriented computer programming techniques involve the definition, creation, use and destruction of software entities referred to as "objects." Each object is an independent software entity comprised of data generally referred to as "attributes" and software routines generally referred to as "member functions" or "methods" or "logic" which manipulate the data.

One characteristic of an object is that only methods of that object can change the data contained in the object. The term "encapsulation" describes the concept of packaging the data and methods together in an object. Objects are thus said to encapsulate or hide the data and methods included as part of the object. Encapsulation protects an object's data from arbitrary and unintended use by other objects and therefore prevents an object's data from corruption. Encapsulation also 'hides' the implementation details, thereby supporting a wide range of possible implementations that result in the same data services and behaviors.

To write an object-oriented computer program, a computer programmer writes computer code that implements a pre-defined model of the system which typically represents 'real world' elements and their relationships. The object oriented-computer code defines a set of "object classes" or more simply "classes." Each of these classes serves as a template which defines a data structure for holding the attributes and program instructions which perform the method of an object. Each class also includes a means for instantiating or creating an object from the class template. The means for creating is a method referred to as a "constructor." Similarly, each class also includes a means for destroying an object once it has been instantiated. The means for destroying is a method referred to as a "destructor."

When a processor of a computer executes an object-oriented computer program, the processor generates objects from the class information using the constructor methods. During program execution, one object is constructed, which object may then construct other objects which may, in turn, construct other objects. Thus, a collection of objects which are constructed from one or more classes form the executing computer program.

Object-oriented computer programming techniques allow computer programs to be constructed of objects that have a specified behavior. Several different objects can be combined in a particular manner to construct a computer program which performs a particular function or provides a particular result. Each of the objects can be built out of other objects that, in turn, can be built out of other objects. This resembles complex machinery being built out of assemblies, subassemblies and so on. Similarly, computer programs can be assembled from different types of objects each having specific structural and functional characteristics. In addition, container objects, heterogeneous aggregate objects the purpose of which is to hold unrelated component objects of multiple unrelated types, may be employed to "contain" further finctionality for use in an object-oriented application.

The term "client object," or more simply "client," refers to any object that uses the resources of another object which is typically referred to as the "server object" or "server." The term "framework" can refer to a collection of inter-related classes that can provide a set of services (e.g., services for network communication) for a particular type of application program. Alternatively, a framework can refer to a set of interrelated classes that provide a set of services for a wide variety of application programs (e.g., foundation class libraries for providing a graphical user interface for a Windows system). A framework thus provides a plurality of individual classes and mechanisms which clients can use or adapt. In one embodiment, the system of the invention is supplied as a framework that a business enterprise can tailor to its particular needs.

An application framework refers to a set of classes which are typically compiled, linked and loaded with one particular application program and which are used by the particular application program to implement certain functions in the particular application program. A system framework, on the other hand, is provided as part of a computer operating system program. Thus, a system framework is not compiled, linked and loaded with one particular application program. Rather, a system framework provides a set of classes which are available to every application program being executed by the computer system which interacts with the computer operating system.

The system and method of the invention may be implemented on a single computer or on a computer network. Generally, a computer network may include any number of computer "machines" which may be actual computers, such as work stations or PCs commonly known in the art or any other computers useful as either server or client machines, or virtual machines. Virtual machines are software devices that operate on a computer but appear to the software that runs on the virtual machine to be a complete computer. A common example of a virtual machine known in the art is the Java virtual machine, however, other types of virtual machines are available and may be used herein. Computers in a computer network implementing the systems and methods of the invention can be connected by a communications network such as a TCP/IP network (including intranets or the Internet), SQLNet, or the like.

Software objects generally run on machines in a computer network. Objects may be created using any object-oriented software programming language known in the art such as C++, Java, Objective C, SmallTalk or others. Additionally, a number of visual and textual software development tools exist to help developers to define and create objects, including Visual C++, Rational Rose, and Persistence. One or more databases are also be provided on one or more machines. The databases may be object-oriented databases or relational databases. The description that follows will generally refer to databases used with the invention as relational databases, however, a person of ordinary skill in the art will recognize that object-oriented databases may be used in place of the relational databases.

The systems and methods of the invention may also be implemented in a distributed object computing environment. A distributed object computing environment is a computer network that uses a communications network known as an Object Request Broker ("ORB"). An ORB is middleware that manages communications and data exchanges between objects, even when those objects are on different machines. The primary functions of an ORB include defining interfaces between objects, locating and activating remote objects, and communications between clients and objects. The goal of an ORB is to make it appear as if an object is local to a client, while in fact the object may reside in a different process or machine. A variety of ORB standards are available for software development including COM/DCOM by Microsoft, the Common Object Request Broker Architecture ("CORBA") organized by the Object Management Group ("OMG"), and the Remote Method Invocation ("RMI") extensions to the Java language/virtual machine. Distributed object applications can be particularly useful for deploying object-oriented software throughout a geographically disparate enterprise while maintaining the performance and feel of a single application to users at any location.

An exemplary business model 100 of the invention for use in the field of health care is shown in FIG. 1. This business model 100 is based on discrete components which represent elements of the health care business that have defined or definable inter-relationships. For example, Clients 102 (or patients) are a source of revenue in this business and the Client's interaction with the business is driven by some medical Problem 104 that the Client has. A Client 102 also consumes Services 106 that are selected and managed by Providers 108 based Problems 104 that the Client 102 has. Services 106 are provided when there is an Encounter 110 between the Client 102 having one or more Problems 104 and a Provider 108 having Services 106. Representative business model 100 is therefore based on these components and their inter-relationships. Because of the shape in which business model 100 is presented, it is sometimes referred to herein as an "H" business model.

Each component of business model 100 has objects which possess certain attributes and behaviors. For example, a Client 102 is uniquely defined by a unique set of data attributes (last name, first name, medical record number, etc.). The Client 102 also know that he or she has a Problem 104 for which he or she seeks the Service 106 of a Provider 108. Over time the Client 102 knows the history of his or her Encounters 110 with certain Providers 108. These components, having attributes and behaviors, can be discretely modeled using object-oriented techniques into objects having data and methods. In particular, each component can be represented as a class, such as a Client 102 class, from which objects that represent individual patients can be instantiated any number of times.

Business model 100 is supported by a data model that can be described using relational data management techniques (i.e., a relational data model). The relational data model can be implemented using a relational database management system (RDBMS). As previously noted, a person of ordinary skill in the art will readily appreciate that objectoriented data management techniques could be applied as well. The RDBMS can acquire the data elements that support the business model from a source such as departmental legacy systems and mapping those data elements into the relational data model of the DBI components. Thereafter, the DBI manages the full life cycle of the data elements.

Figure 2:
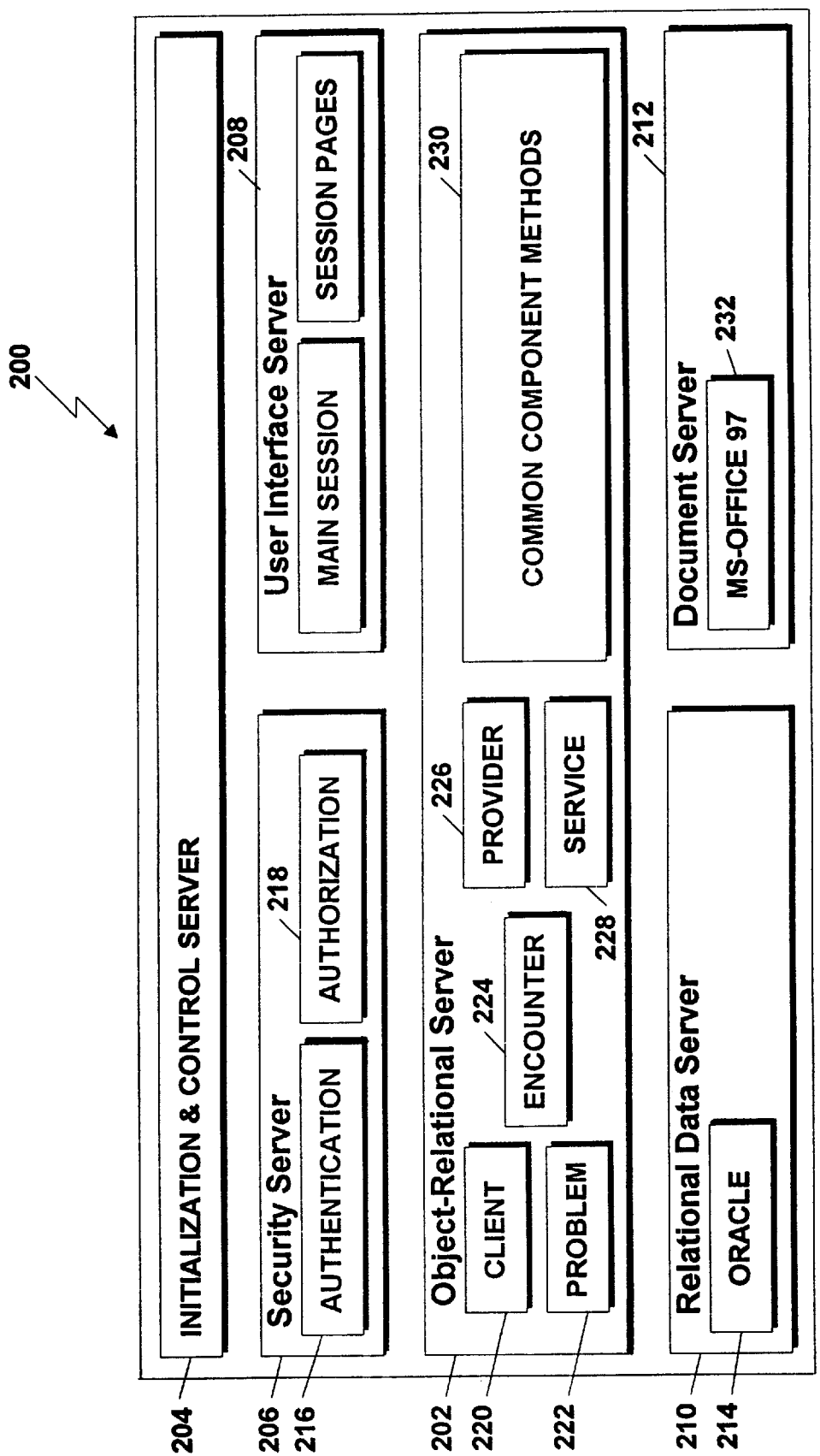
FIG. 2 illustrates a database infrastructure server architecture that implements the business model of FIG. 1.

A DBI server architecture 200 for a database infrastructure of the invention is illustrated in FIG. 2. Consistent with the object-oriented approach, the physical structure of the DBI server 200 need not follow the functional structure illustrated in FIG. 2, rather, each "server" (and particularly the Object-Relational Server 202) may be an object or collection of objects that perform the necessary functions and those objects may run anywhere within a given computer network. The DBI server 200 can include an Initialization & Control Server 204, a Security Server 206, a User Interface Server 208, an Object-Relational Server 202, a Relational Data Server 210 and a Document Server 212.

The Initialization & Control Server 204 initiates the DBI application and controls the presentation and cursor functions. The Initialization & Control Server 204 also controls calls to the Security Server 206 to allow access to the DBI application only to authorized users and establishes connections to the relational database management system (RDBMS) 214 that implements the Relational Data Server 210.

The Security Server 206 authenticates 216 users at login. In one embodiment, the Security Server 206 runs on a WindowsNT server that may be dedicated to running the Security Server or it may share resources with other applications. The authentication may be provided by a commercially available product such as SecurID from Security Dynamics, Inc. The Security Server 206 can provide a two factor (or strong) authentication service. Such a service requires a user to enter a character string that combines something that the user knows but should keep secret (i.e., a password) and something that the user has (e.g., a string that is randomly generated by the Security Server 206 for this purpose). Once the user is authenticated, the DBI Server 200 determines whether the user is authorized 218 to view data. This authorization may be performed at the Security Server 216, however, the RDBMS 214 used by the Relational Data Server 210 may provide such services.

The User Interface Server 208 defines the initial window display that is opened by the DBI application after the user is authenticated by the Security Server 206 and supports the manipulation of the application window by the users. The User Interface Server 208 then displays session pages (DBI windows) that are opened by the user. Following a successful user login, an initial session page is automatically opened. Each session page displays the "H" business model such as that shown in FIG. 1 having client, problem, encounter, provider and service components. Each component is ready for interaction with the user.

The Object Relational Server 202 defines the attributes and the behaviors or methods of each of the core components in the business model that is implemented in the DBI application and displayed on the DBI session page. The Object Relational Server 202 also serves as a "container" for additional components that may be developed in the future to interact with the core components of the business model in response to future market requirements. In our health care example, additional components can include, for example, outcomes, document, and financial components. The structure and design of the DBI Server 200 and Object Relational Server 202 allow for rapid deployment of additional business model components or modification to attributes or behaviors of existing components as required.

Each business model component is supported by a corresponding component server within the architecture of the Object Relational Server 202. For our health care example, a client component server 220, a problem component server 222, an encounter component server 224, a provider component server 226, and a service component server 228 are provided. Each component server defines the object oriented characteristics (i.e., the attributes and methods) of its respective component as well as the relational data model that is implemented in the Relational Data Server 210 by a relational database management system to support them. The relational data model of each component maps the data attributes of the respective component to data elements that the DBI application acquires from departmental sources (e.g., patient registration, appointment schedulers, laboratory applications, etc.). Each component server also contains scripts for creating RDBMS tables that implement the relational data model and load the source data into the tables.

The Object Relational Server 202 also includes a Common Component Methods server 230 that performs generic functions which might be used by more than one component. Such generic functions can include temporal services (e.g., support of timeline display and function, computation of time intervals), list and edit services (e.g., manipulation of lists, display of property sheets), drag and drop services for manipulating user interface elements, object container interface for interfacing with other objects (e.g., OLE containers for interfacing with OLE objects), calender, list, mouse control, tabbed "select" boxes, component buttons & graphics, data stream formatting, and graphical objects. OLE is a Microsoft technology upon which COM, DCOM and Active-X are built to provide higher level application services such as object "linking" and "embedding" that are used to create compound documents generated from multiple tool sources which extend to the Internet.

The Relational Data Server 210 performs the relational database management services that are required to support the functions of the DBI servers 210. In one embodiment, the Relational Data Server 210 comprises an Oracle RDBMS running on the Solaris operating system available from Sun Microsystems. The same DBI architecture may be implemented using other RDBMS systems, including for example Sybase or Microsoft SQLServer, or using another operating system, including for example WindowsNT.

The Document Server 212 links to and serves up documents to the DBI application's components. Document Server 212 is a "container" of simple word-processing, spreadsheet, presentation graphics, and image documents as well as comprehensive document management systems that serve and manage the full life cycle of multi-modal document authoring, publishing, distribution, and viewing. In one embodiment, the Document Server 212 comprises Microsoft Office 232 so as to serve up Microsoft Word word-processing documents and Microsoft Excel spreadsheet documents.

The Gateway Server (not shown) can also be provided to serve as a link to departmental applications for loading source data into the RDBMS 214 to support the data model of each component in the business model.

Figure 3:
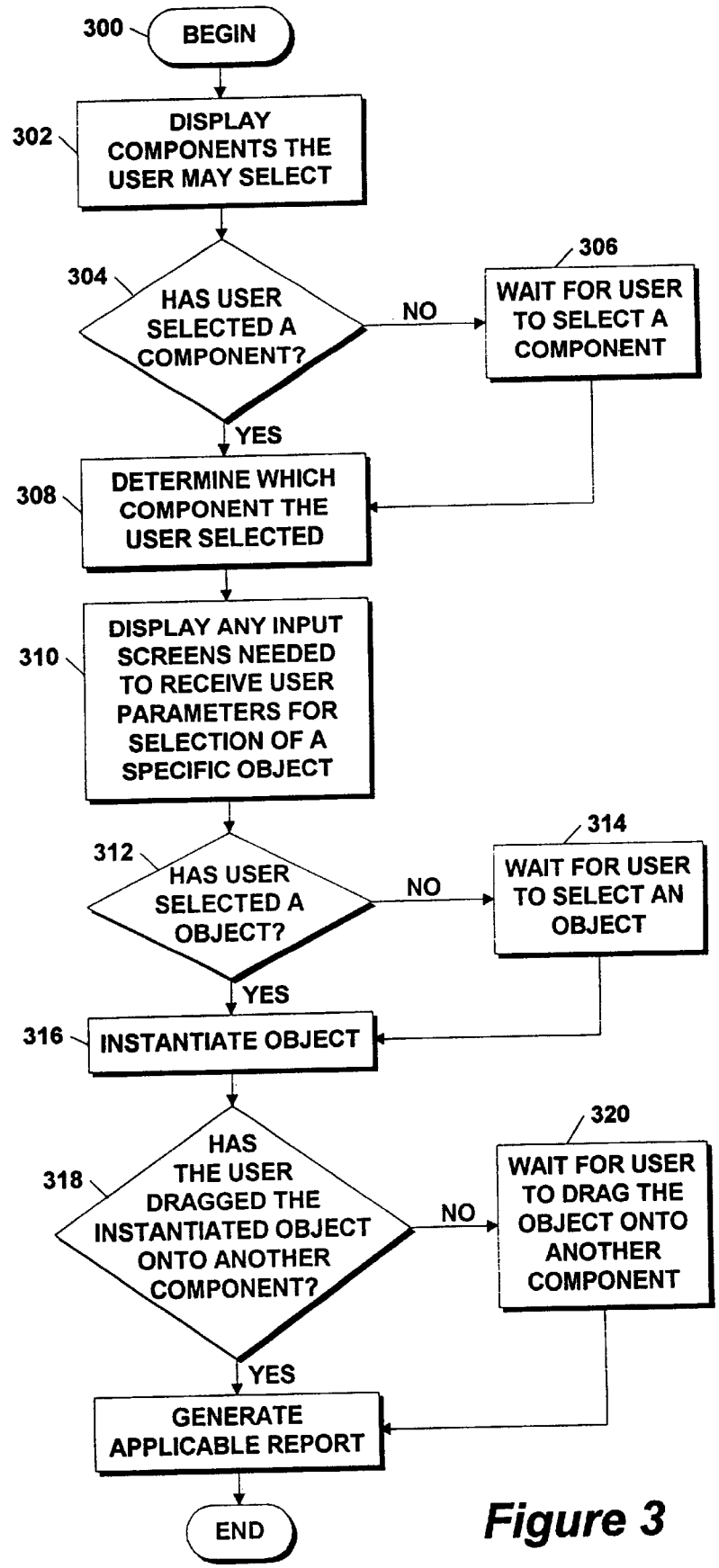
FIG. 3 illustrates the process flow for a method of user access to a database infrastructure of the invention.

A method of the invention for employing a visual interface to allow user access to business data is illustrated in the flow chart depicted in FIG. 3. If desired, the method may begin 300 only after a user has logged on to the system by supplying a user name and pass code. After authorization, the system displays components of the business model for the user to select 302. This display may be of the "H" form illustrated in FIG. 1 for a health care business model. The software application waits 304, 306 until the user has selected a particular component of the business model, then determines 308 which component the user has selected. The software application next displays 310 any input screens or GUIs needed to receive user parameters for selection of a specific object of the type represented by the selected component, and waits 312, 314 for user selection.

Once a user selects a particular object (e.g., selecting a particular patient object within the client component), that object is instantiated 316. Generally, instantiation involves execution of a method by the object that submits a query to the relational data server 210 for execution by a RDBMS 214. The RDBMS 214 sends the result of that query in the form of a group or stream of data elements to the object. When the object receives the data elements, it formats them (e.g., arranges the data in a list, produces a graphical timeline, etc.) and presents it to the user. Components may execute these same methods to provide lists of data representing individual objects for the user to select from a GUI in step 310.

The instantiated object is displayed to the user in graphic form and the software application waits 318, 320 for the user to drag the object, likely by selecting the object display with a mouse and dragging the object display across the screen, onto another component. Dragging an object to another component generates a report 322 showing the relationship between that object and that component. For example, dragging a client object representing a particular patient to the problems component will generate a report showing all of the problems reported by that patient. These are problem 'objects'. The user could, for example, activate one of those problem objects to view detailed reports on that particular problem for that patient or drag and drop the problem object on the client component to generate a report showing all clients who had the same problem.

Providing a visual display of a number of components and manipulating those components by clicking, dragging and dropping forms the basis of a "user-centric" interface architecture supported by the DBI. Of course clicking, dragging and dropping commonly performed using a mouse at a personal computer or work station are only one way to implement the user-centric architecture of the DBI visual interface. A voice recognition interface, for example, could also be employed to allow a user to speak the name of the component to instantiate, select a particular object to instantiate, and manipulate that object by speaking the name of the component that the user wishes the object to interact with. Other elements of the user-centric architecture include commonality of interface features to perform common functions with different components. For example, Visual User Interfaces for selection of a particular object from each component can be similar, each using drop down lists or menus to allow selection of a name for a particular field, and using the same, for example drag and drop procedures for manipulating any object to interact with any component. In addition, the use of the "H" model can provide intuitive visual clues that allow even a novice information technology user to readily use and manipulate objects and components representing elements of the business model and underlying data structures with minimal training.

The system of the present invention will now be described with reference to its organization and operation for use with a client medical records database in a healthcare organization, such as a health maintenance organization, hospital, or other such entity based on the business model structure displayed in FIG. 1.

Generally, the system operates to identify an individual object from a group of components that make up a business model and to display data or relevant records for that object. Its organizational structure is also useful for identifying medical problems, or clusters of problems and quickly viewing or comparing their characteristic presentations, treatments, and susceptible populations. It thus lends itself both to medical records accessing for the immediate use to admit, diagnose and treat a particular patient, and also to study or evaluate institutional or medical aspects of particular conditions or of the provision of medical services for particular conditions. Implementation of the invention will best be understood by a detailed discussion of an embodiment as viewed by an operator during use of the system for identifying an individual patient and accessing relevant records.

The system operates with a display screen and work station, wherein a series of displays and operator queries are provided under programmed control to guide and expedite the retrieval of appropriate records and information. In general, these screens are arranged with pop-up menus, windows and buttons for prompting the user to enter, select or confirm particular pieces of data, and the system provides interactive screen software allowing the user to select data and to "drag and drop" data to select various branches or modules of the system during operation to control the search for and display of information.

Figure 4:
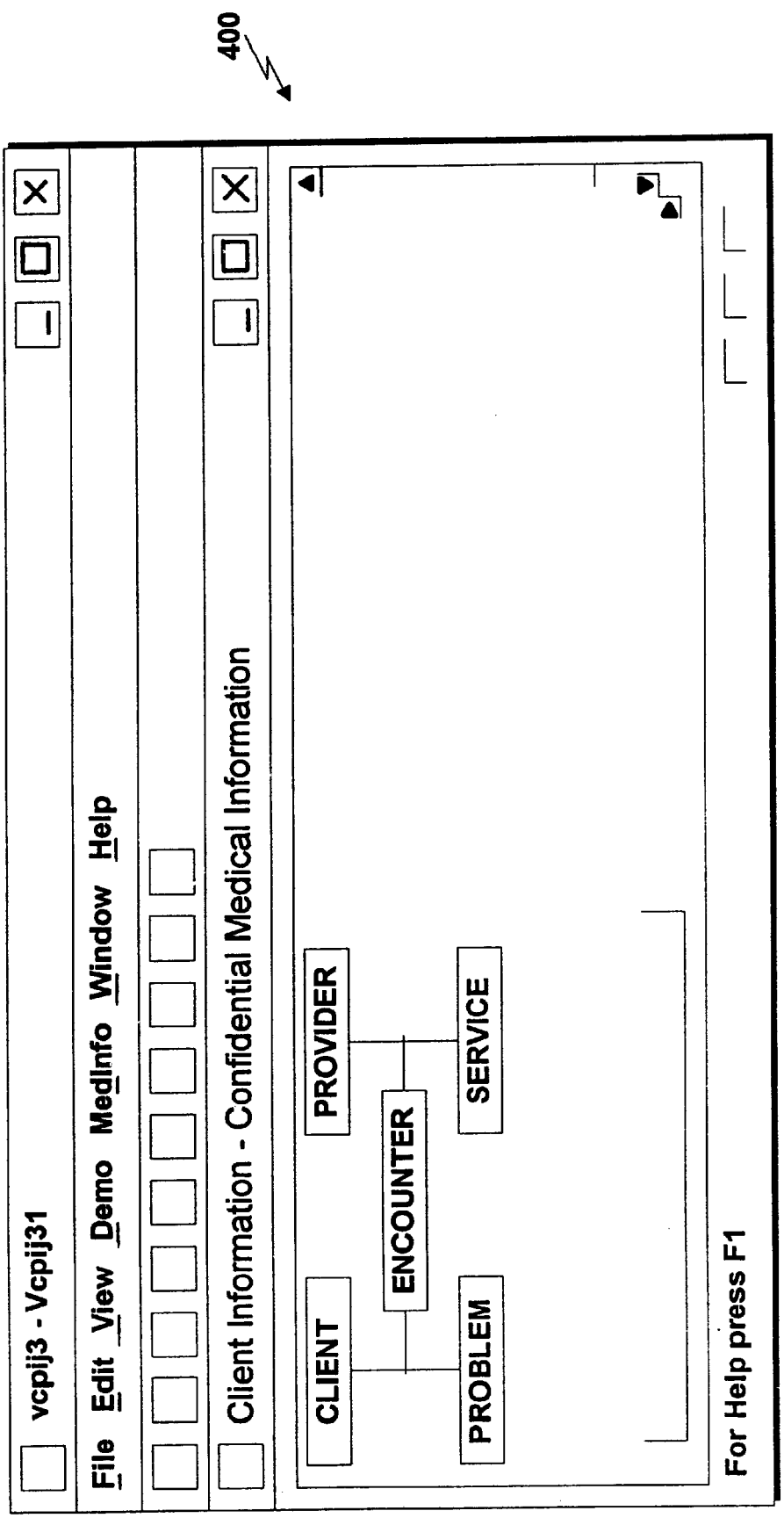
FIG. 4 illustrates an exemplary entry screen for a user accessing a database infrastructure representing the business model of FIG. 1.

As illustrated in the opening screen display 400 of FIG. 4, the basic system organization involves a set of five business model components organized by CLIENT, PROBLEM, PROVIDER, SERVICE, and the ENCOUNTER of a client with the healthcare enterprise. These five areas of information allow the operator to identify the necessary records starting from any one of these five areas, offering significant advantages to different operators within the health care system, as discussed further below. Thus, for example, the CLIENT component includes modules for determining and accessing the names of all patients together with identifying information regarding those patients such as age, sex, condition, social and other data. Its operation facilitates the identification of the client starting from entry of partial information, such as name or phone number, and may greatly expedite tasks such as intake registration or correspondence. The PROBLEM component includes the medical conditions and related data for the clients. The PROVIDER component includes names, profile and indices to identify and access provider records of the various healthcare professionals involved in providing services, and the SERVICE component contains similar information for the diagnostic procedures, treatment and other services provided. The ENCOUNTER component includes records of each visit or communication with the institution, its various clinics and providers, and is organized to provide relevant information for that structural division.

In one typical mode of operation, the operator proceeds to select or enter information in a series of steps to identify a particular client and then access relevant information or specific records from any or all of the other four component areas. Operation of the system will now be described with respect to such a typical presentation.

Figure 5:
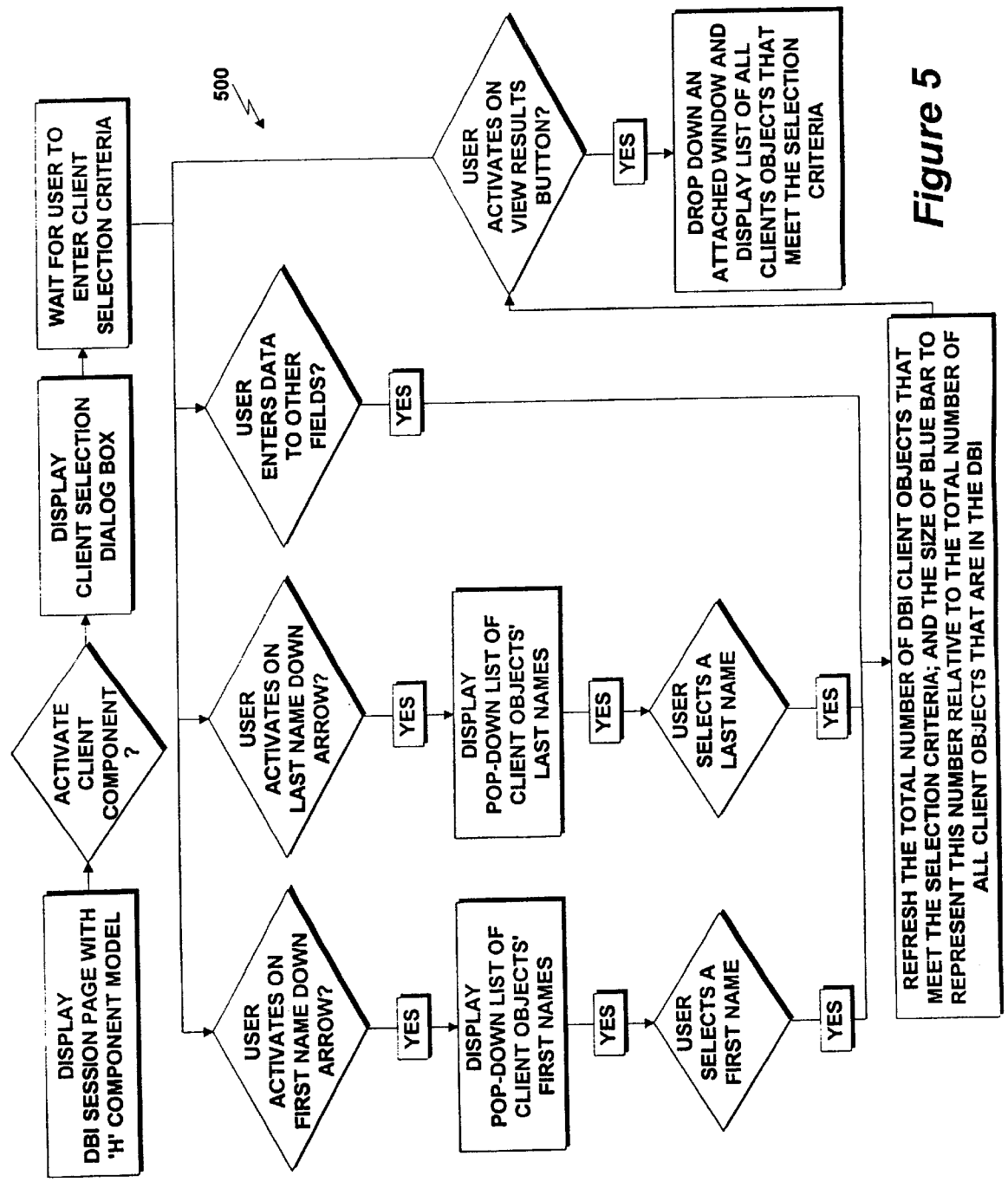
FIG. 5 illustrates a user interface process flow for selecting and instantiating one element of the business model presented in FIG. 4 by selecting a particular "client"

To access the data base using client data the operator clicks on the CLIENT button, and this calls up a CLIENT data screen in which various objective data about the client such as first name, last name, sex, age, date of birth or client ID number may be filled in. An exemplary process flow 500 for selecting a client is illustrated in FIG. 5 and an exemplary client data screen 505 in FIG. 5A. The description that follows refers generally to that process flow 500 and data screen 505. Preferably the screen 505 displays the total number of clients recorded in the database, and as each piece of data is filled in, shows the number of potentially matching clients who still meet the specified data criteria. Furthermore, the windows for entry of such data are preferably equipped with scroll button and a dictionary-type search engine so that after typing the first few letters of a client name, for example, the operator may automatically scroll among the comparable names in the database to select one that matches.

Thus, for example, after typing in "Jo" in the first name entry box, the program displays the potential matching names "Joan, Joanie, JoAnn, Joanna, Joanne, Jose . . ." allowing the operator to select an appropriate one. When the presenting client is an existing client in the database, this provides a safeguard against slight misspellings of the name, and in connection with the features described further below also allows the operator to identify other records wherein the name may have already mis-spelled. As each piece of information is entered, the selection module determines the set of client names matching the entered data and a window at the bottom of the screen displays the number of records potentially matching the input data. Thus, in the given example, if the first name is Jose, there may be only four individuals out of the initial thousands. By clicking on a VIEW RESULT button on the screen 505, the client identification data for these individuals is displayed in a list so that the operator can see the first and last names, gender, birth date, address and/or other standard information matrix. These are client objects that can be further activated or manipulated similarly to activating and manipulating other objects as previously described.

Display screen 505 is preferably organized so that the list of potential matches is displayed in columnar or spreadsheet form by the entries such as last name, first name, birth date and the like. Preferably the module operates to sort a given column when the operator clicks on the header of that column. Thus, for example, the potential matches may be sorted alphabetically by last name, or by age or the like. Similar list narrowing or sorting occurs with each data entry, so that for example the operator may enter first name and month of birth, or two other pieces of information, or the client ID number or partial ID number. When the data types are potentially conflicting (e.g., when the operator enters both the age and the date of birth) the module preferably accepts only the last-entered datum of the pair, so as to avoid drawing a null set when mutually exclusive conditions are inadvertently entered. In a few steps this data entry procedure results in the identification of a single client and one client object with a client name on it is created. This further illustrates the invention of the usercentric visual interface which interactively guides the user through the selection process.

Figure 6:
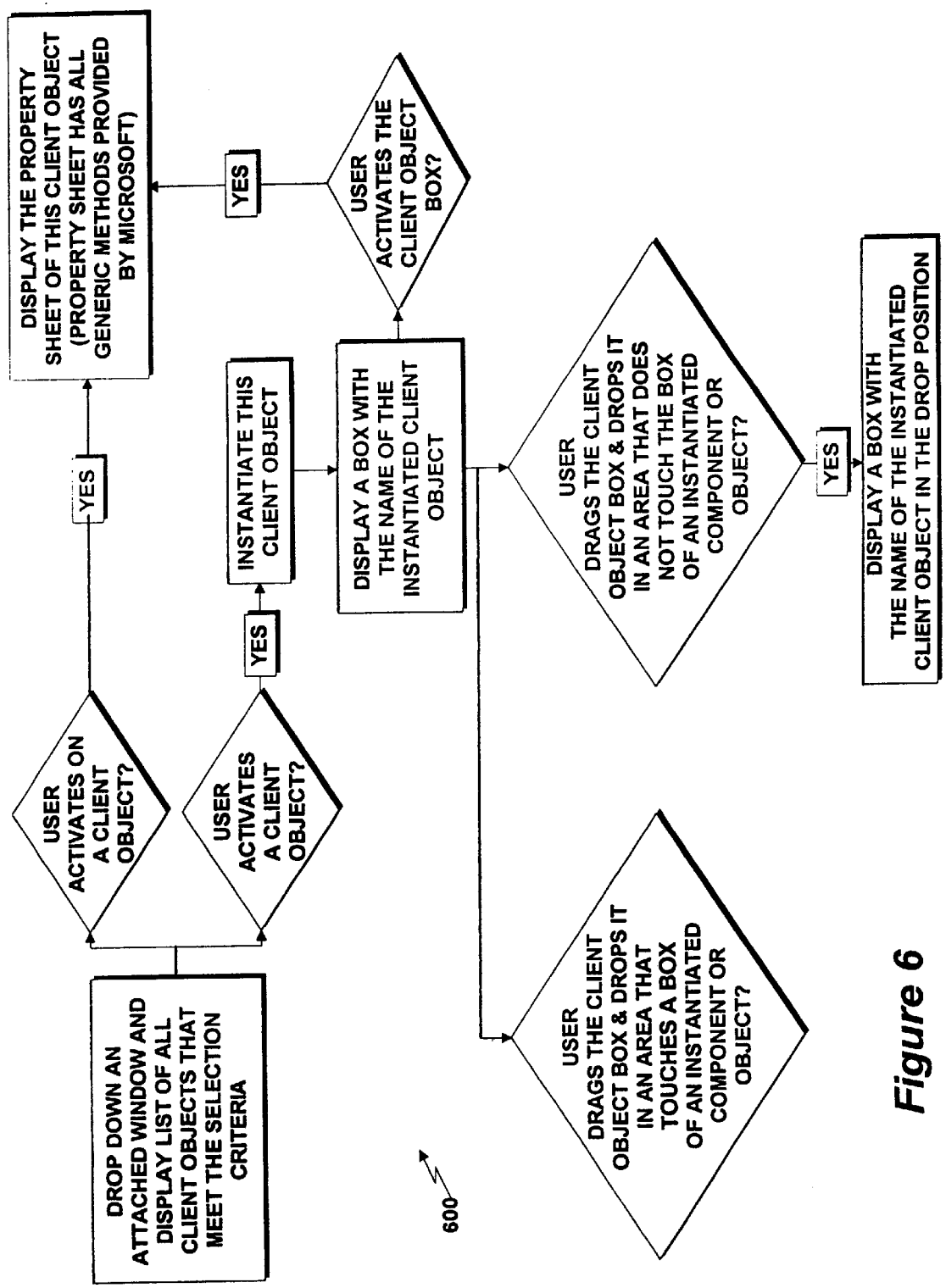
FIGS. 6 and 7 illustrates a user interface process flow for manipulating the instantiated element of FIG. 5.
Figure 6A:
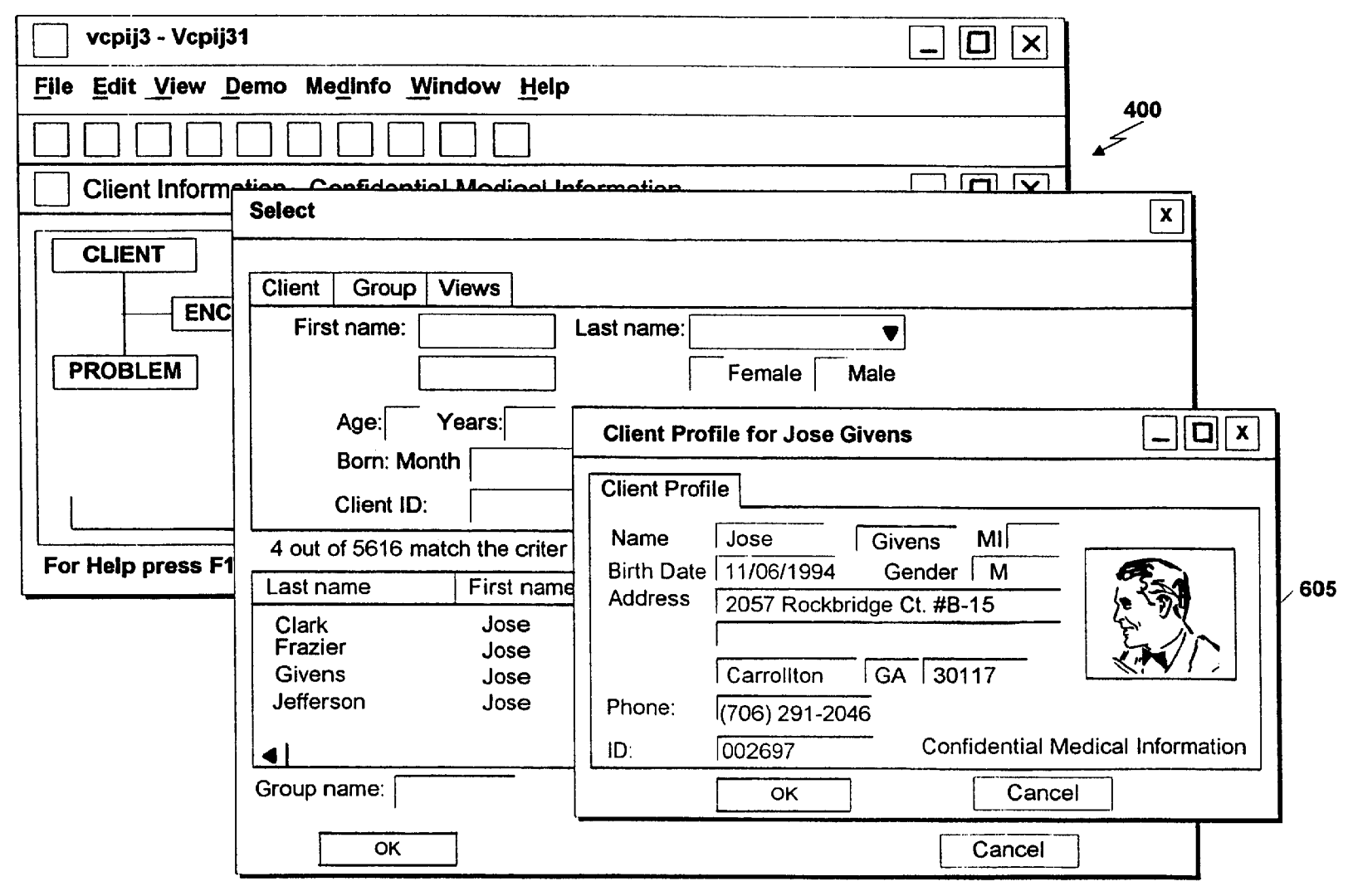

At this point, illustrated by the process flow chart 600 of FIG. 6, if the operator knows which of these clients is the correct one, that client may be selected by double clicking on the client name, or selecting and hitting the ENTER button or clicking the OK button. In one embodiment of the system, the profile is selected by right clicking on the last name of the listed client to bring up a profile box 605 (FIG. 6A) which may for example include resident's address, telephone, patient and/or social security ID number, a photo of the client, and the like. In addition, a user may bring up multiple profile boxes before selecting one as the client of interest.

Figure 7:
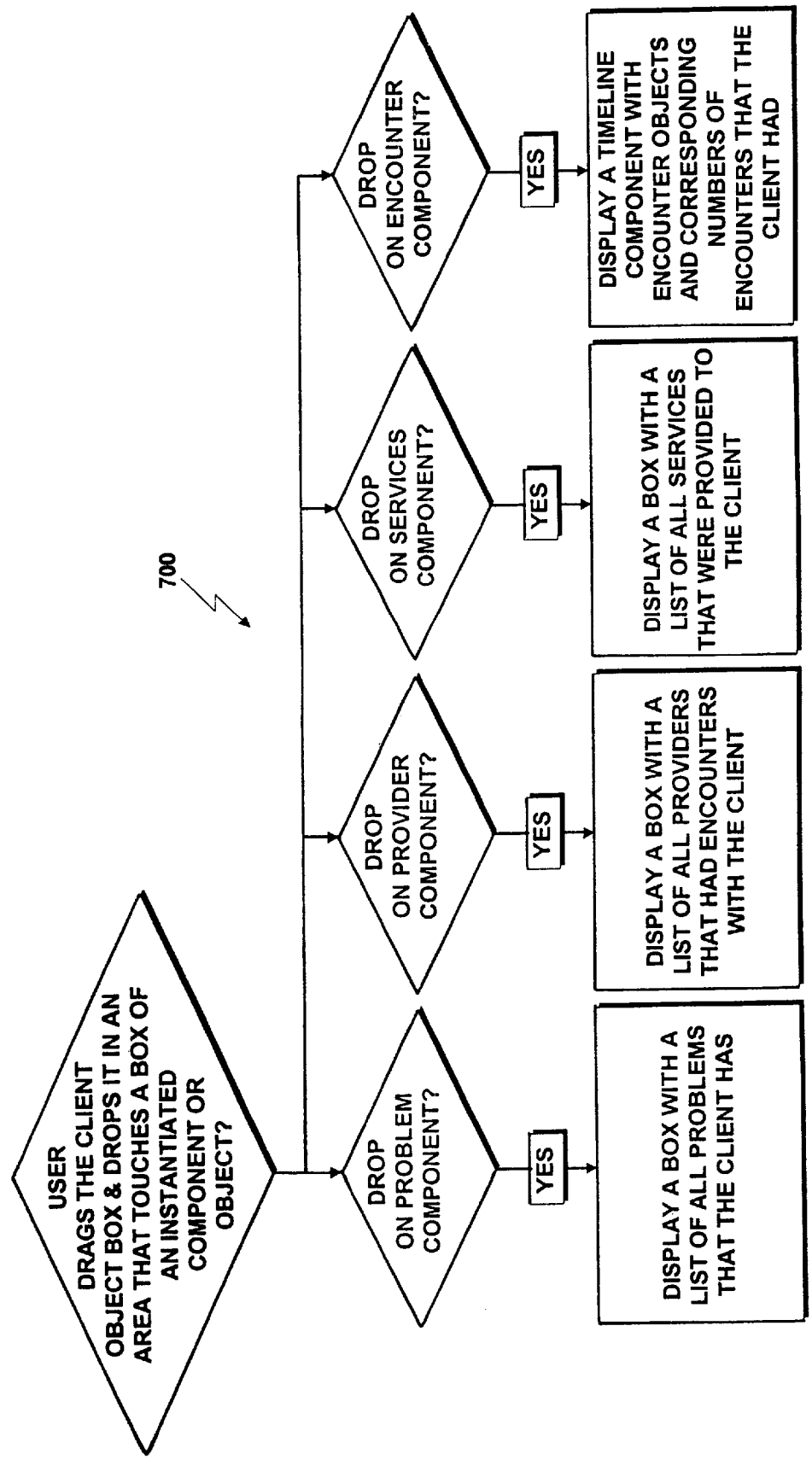

The client having been identified, a client object representing the selected client is instantiated and an object box having the client object's name is displayed over the CLI- ENT graphic of FIG. 4. The user may then drag and drop the client identification on any of the other four displayed component boxes to access data through organized relational queries for the client PROBLEMS, system ENCOUNTERS, PROVIDERS and SERVICES provided with regard to that particular client object. When, as illustrated in the process flow chart 700 of FIG. 7, the client object is dropped in an area that touches one of these four boxes, a display screen pops up with a list of the respective problems objects, encounters objects, providers objects or services objects from the database for that client object.

In a particular embodiment, the initial display screen for each of the five components is arranged in a graphic form to allow the quick identification of the selected data such that by clicking on a displayed screen area, a piece of information and relevant profiles or actual records are called up, preferably in their instantiated object form. Thus, for example, a time line may be displayed indicating the encounters with the healthcare enterprise under the ENCOUNTER component. Under the PROBLEM component, a box may be displayed with a list of all problems that the client had, or a list of problems ordered by initial presentation or otherwise visibly organized. Similarly, the PROVIDER component screen may display a list of providers, and the SERVICES component screen may display a list of services provided to the client.

Figure 8:
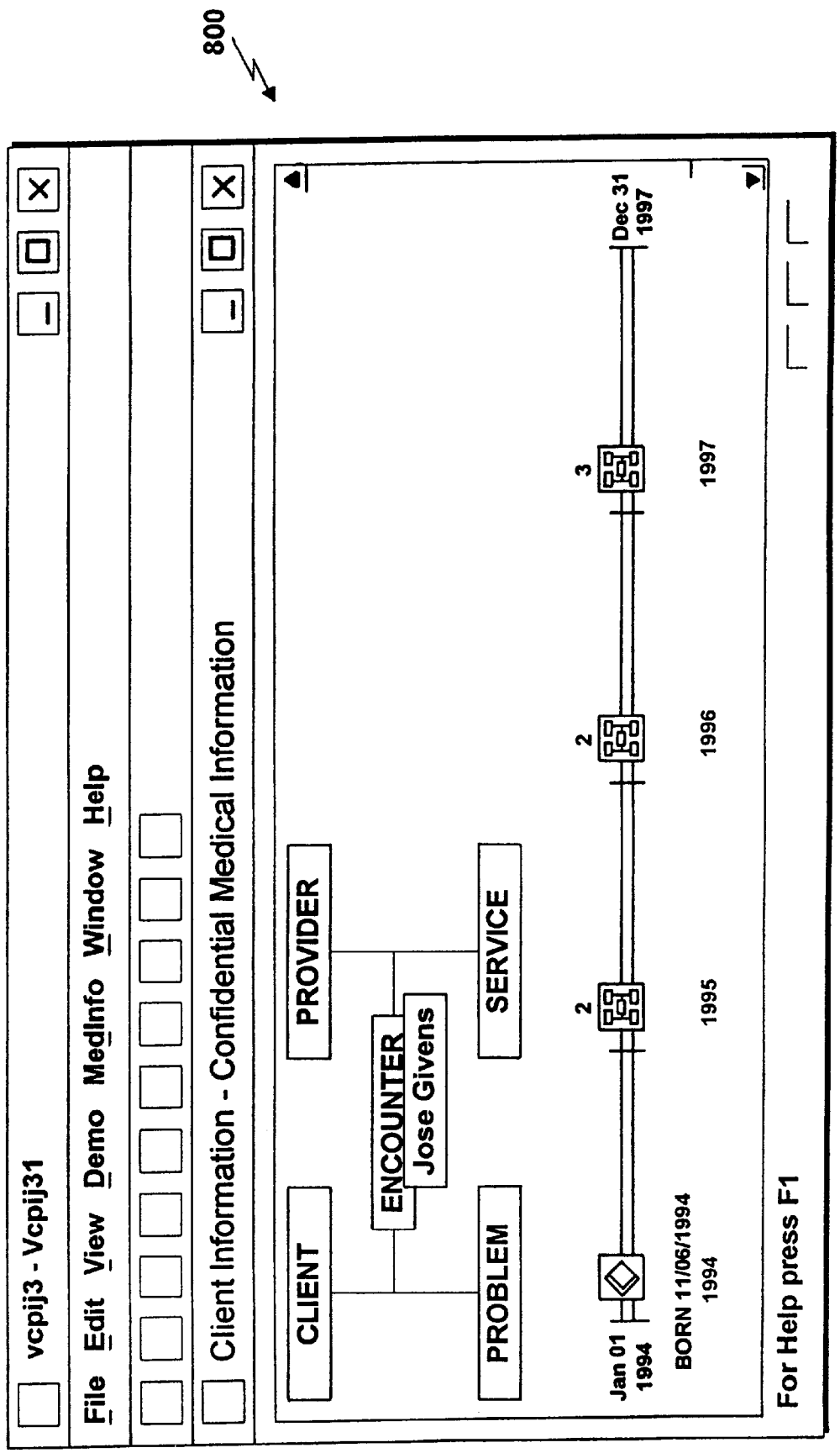
FIG. 8 illustrates a timeline report screen of encounters generated when a user manipulates the instantiated element as shown in FIG. 7 to cause the selected and instantiated "client" element to interact with an "encounter" element.

FIG. 8 illustrates an initial ENCOUNTER report screen 800 for the selected client ("Jose Givens"), wherein a time line encounter object conveniently summarizes or outlines the data on encounters available in the database. As illustrated in that screen 800, the client was born in 1994, had two encounters in each of the following two years and three in the third year. The user may obtain further details of each encounter or appearance at the healthcare enterprise by clicking at the appropriate screen position on the displayed date of encounter. When there is more than one encounter in a year, the operator may click again to explore an encounter page display for each successive one of the encounters.

Figure 9:
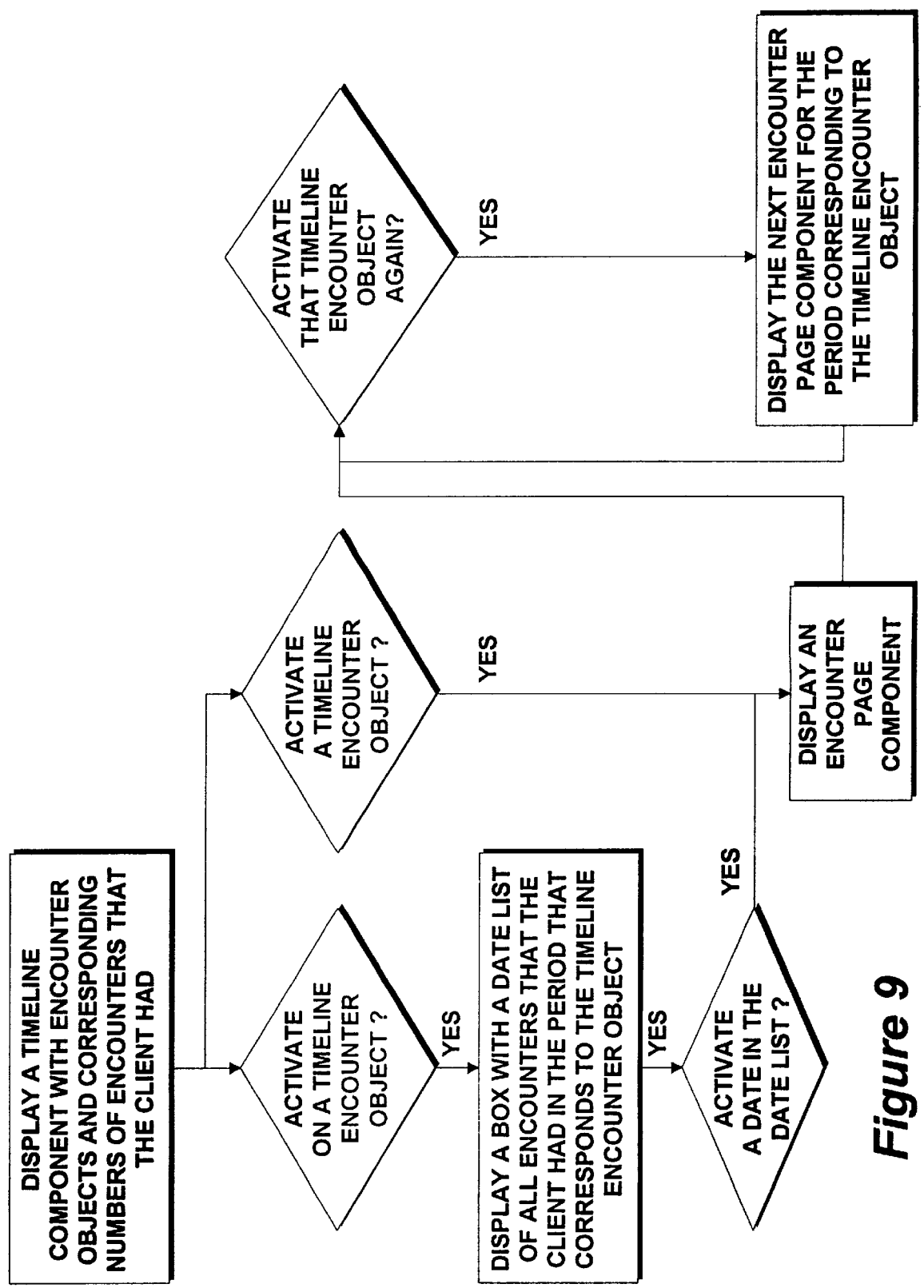
FIGS. 9 and 10 illustrates a user interface process flow to allow the user to select, instantiate, and view reports on a particular "encounter" element for the previously selected "client"

As illustrated in flow chart 900 of FIG. 9, this user request then instantiates an object for this encounter and displays an encounter page report screen 905 (FIG. 9A) including a profile of the activity and information from that encounter with the institution. By way of example, encounter page display 900 may include a listing of the problems noted at that encounter, the service provided such as counseling, medication or referral, and the providers involved. Preferably the screen is provided with a plurality of index tabs related to that encounter and accessing either a profile, or the documents generated at that time. These may include documents such as a client encounter form summary; a detailed client encounter form; in the case of a child, a developmental pediatric initial evaluation or follow-up; notes of a phone encounter; records of a confidential psychological evaluation or family social history assessment; team interdisciplinary evaluations or follow-up; therapy evaluations or progress notes; and medical or behavioral needs screening assessments.

A separate listing of providers is displayed for each encounter, and this is indexed to allow the diagnoses or records of each provider made at that encounter to be called up and accessed. Thus, by dropping the client's name in the ENCOUNTER component, a display of the medical history as organized by that component is immediately made accessible through the system for that encounter and for each subsequent encounter upon which the operator clicks.

Figure 10:
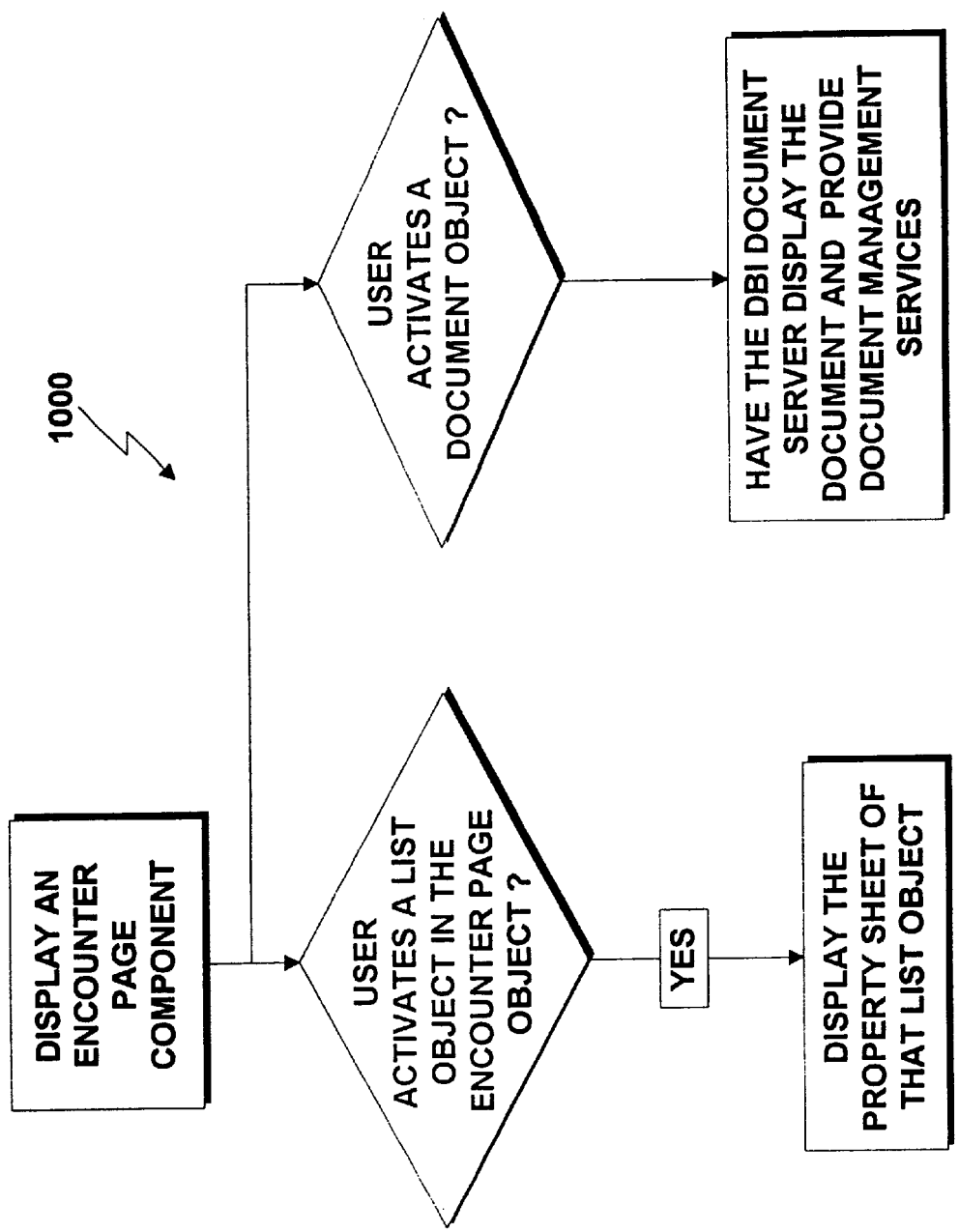

As shown in flow chart 1000 of FIG. 10, the operator monitor displays in general allow the user to activate a list object on the ENCOUNTER page and display the property sheet of that list object, or activate a document object and have the document server display the document and provide document management services for accessing, annotating or linking those objects.

When clicking to display the property sheet of a list object, the system displays basic information about the identified item. Thus, for example, when clicking on a problem such as the developmental delay problem shown in encounter screen display 905 (FIG. 9A), the property sheet would list information such as a degree of disability, its type (e.g., syndrome), its ICD-9 classification number and the like. When activating the profile sheet might list the name, identity and medical or academic qualifications of the professional provider, the provider identification number, department and location and other such profile information. When calling forth the profile sheet on a service such as a psychological diagnostic evaluation, the profile would list information such as the name of the service, the type such as particular test sequences administered, and the CPT code or related data. The nature of displayed information may involve descriptive charts or spread sheets indicating involvement of equipment, services, professional staff, facilities, activities and institutional resources, or various plans, client "contracts" (in a government social services context) or even forms or data for reimbursement, insurance, payment or care. Where the information to be displayed is in the form of a spreadsheet or word-processing document, the system displays this information by calling up a spreadsheet application such as Microsoft Excel or a word-processing application such as Microsoft Word, which are activated as appropriate when the user requests a display of such information. Thus, for example, if the operator clicks on the family social history assessment document, the program starts Microsoft Word if it is not open, opens the document and fills in the client demographic information and associated encountered data from the database to display the appropriate completed assessment form and data.

Thus the system operation allows the identification of client, encounters, the records associated with each problem, provider, service and surrounding reports and institutional activity, to be readily identified, viewed in summary, and accessed from the database.

In the preferred embodiment, during this process the basic five-component index screen for the CLIENT, PROBLEM, ENCOUNTER, PROVIDER and SERVICE remain displayed or minimized on the window, and the operator may select another client by clicking on the CLIENT component to start client selection process from the beginning again.

In addition to the ENCOUNTER component, each of the other four components are organized in a structure to logically track and utilize the records and information in those areas. Thus, by dropping the identified client name in the PROBLEM component, a PROBLEM screen is called up listing each of the client's problems, together with related information such as a category, type, frequency, date of first diagnosis and the like, and each of these may be sorted within its category by clicking on the category heading, or further information on the particular problem may be displayed by clicking on the problem name. Preferably each problem has associated with it a problem profile as described above, allowing the physician or other operator to quickly determine the problem's history, status, prognosis and relation to other problems or conditions.

By dragging and dropping the client name in the SERVICE component, a complete list of services provided to that client is displayed, broken down by the service name and type and listing the frequency and first time for each service. By clicking on an entry a profile is displayed for that entry indicating the service type, location where provided, CPT code and other such information together with a service description. The service description may include a service line modeler, (displayed in Microsoft Excel when clicked by the user) or a service description (displayed as a Microsoft Word document when requested by the user).

Finally, by dragging and dropping the client name in the PROVIDER box, a list of all providers together with their function, title, department, frequency of visit and first time of involvement are displayed on a PROVIDER screen which again allows the operator to open provider profiles and access more detailed records, reports and other appropriate information from that component.

Similarly, a user could begin the process by selecting an object of any other component (PROBLEM, PROVIDER, SERVICE, or ENCOUNTER), and access desired information by dragging and dropping that object onto any other component. For example, the "developmental delays" PROBLEM object could be selected and dropped on PROVIDERS to see all providers who have treated this problem, CLIENTS to see all patients who have this problem, SERVICE to see all services provided for this problem, or ENCOUNTERS to view every encounter that the healthcare enterprise has had with this problem. Thus, the DBI architecture and user-centric interface allow access to medical records in an immediate manner and allow cross-referencing of the necessary healthcare data to present information appropriate for all healthcare enterprise operations, including billing, diagnosis, treatment, emergency interventions by involved health personnel, as well as facilitating the overall planning, tracking and modeling of treatment and care planning for the individual. The nature of the system allows protection of confidential documents and allows individual operators in particular branches to access profiles necessary to perform care and service planning in an organized and rational order.

For example, in an Internet embodiment in a home-health care organization, the member of the care team who visits a patient in his or her home can connect to the Internet, review the information of this patient, and document the visit using the Internet version of the DBI's visual user centric interface. The patient can review the state of his or her health in comparison to outcomes objectives relative to his or her problems, care plans, and services.

The component-based database infrastructure and user-centric visual interface are fundamental to providing the benefit of making only one or some of the components active in a particular implementation. For example, the home-health care organization may choose to only activate the CLIENT component for use by its patients. In this situation, the patient is authorized to select only his or her CLIENT object, and drag and drop that object on any other component in order to view the respective information exclusively relative to him or her. Because the PROVIDER component is not activated, the patient can't drag and drop one of his or her providers on the CLIENT component in order to view all the other clients that this provider served, or drag and drop one of the services that he or she received on the PROVIDER component in order to see all the providers that provide that service. Respectively, the cost of using the DBI is reduced. This situation illustrates how the component-based database infrastructure and user centric visual user interface enable the organization to customize its business, services, products, and resources to very specific situations.

The DBI architecture and user-centric interface of the invention can be applied to variety of industries other than healthcare. Any business that can be modeled with a number of core components having defined or definable inter-relationships can employ the system of the invention to present those core components to a user in an object-oriented manner to provide the benefits described herein. For example, financial and accounting services businesses can be modeled using CLIENTS, ACCOUNTS, SERVICES, ACCOUNTANTS, and ENCOUNTERS components; an automobile manufacturing business could be modeled using CARS, ASSEMBLY LINES, PARTS, WORKERS, and PROCEDURES components; and a restaurant business could be modeled using GUESTS, MEALS, MENU ITEMS, and WAITERS components. In addition, many such models can be rapidly developed by modifying existing models such as the healthcare model presented herein. For example, the PROVIDER component of the healthcare model can readily be adapted for use as an ACCOUNTANT, WORKER, or WAITER component in these other businesses. Once the industry specific business model components are finalized, the DBI architecture can similarly be reused by adapting it to the new components.

As indicated heretofore, aspects of this invention pertain to specific "methods" and "method functions" implementable on computer systems. Those of ordinary skill in the art should readily appreciate that computer code defining these functions can be delivered to a computer in many forms; including, but not limited to: (a) information permanently stored on non-writable storage media (e.g., read only memory devices within a computer or CD-ROM disks readable by a computer I/O attachment); (b) information alterably stored on writable storage media (e.g., floppy disks and hard drives); or (c) information conveyed to a computer through communication media such as telephone networks. It should be understood, therefore, that such media, when carrying such information, represent alternate embodiments of the present invention.

It will be understood that the foregoing is only illustrative of the principles of the invention, and that various modifications can be made by those skilled in the art without departing from the scope and spirit of the invention.

What is claimed is:

1. A system for accessing business da stored in one or more databases by a user comprising:

a) a display presenting a user with a plurality of components, each component representing a discrete element of a business model, having a defined relationship with each of a plurality of other components of the plurality of components, and including a plurality of information objects, each information object representing an instance of the component business element;

b) a user input device responsive to manipulation by a user to select a first one from among any of the plurality of components;

c) a user input device responsive to manipulation by a user to select a first one of the plurality of information objects from the first component;

d) software including control logic instantiating first information object from data stored in the one or more databases;

e) a user input device responsive to manipulation by a user to cause the first information object to interact with a second component selected from among any of a plurality of component other than the first component, the second component being selected from any one of the plurality of components other than the first component; and f) control logic generating a report showing information objects of the second component which represent instances of the second component related to the first information object.

2. The system of claim 1, further comprising:

g) a user input device responsive to manipulation by a user to select a second information object from the set of information objects shown in the report.

3. The system of claim 2, further comprising:

h) control logic instantiating the second information object from data stored in the one or more databases.

4. The system of claim 1, wherein the plurality of components comprises at least three components.

5. The system of claim 1, wherein the plurality of components comprises at least five components.

6. The system of claim 5, wherein the components comprise client, problem, encounter, provider and service components to support a healthcare business model.

7. The system of claim 1, wherein an instantiated first information object is provided on the display and the user input device responsive to manipulation by a user to cause the first information object to interact with a second one of the plurality of components comprises a pointing device and control logic allowing the user to point to the first information object on the display and drag the first information object across the display to the second component.

8. The system of claim 7, wherein interacting a first information object with the encounter component generates a timeline report of encounters relating to the first information object.

9. The system of claim 1, further comprising a database infrastructure for implementing a relational data structure for supporting the business model, the database infrastructure comprising:

a) a relational data server for processing relational database requests;

b) an object relational server including a number of component servers at least equal to the number of components in the plurality of components, each component server corresponding to one of the plurality of comforts of business model and including means for communicating the relational data server to provide data services for its respective component;

c) a user interface server for displaying the components of the business model to a user and for supporting user manipulation of the components.

10. The system of claim 9, wherein the object-relational server further comprises a common component methods server for performing generic functions used by more than one component.

11. The system of claim 9, further comprising a document server for serving documents to the component servers.

12. The system of claim 11, wherein the document server includes means for viewing a word-processing document.

13. The system of claim 11, wherein the document server includes means for viewing a spreadsheet document.

14. The system of claim 9, further comprising a security server to authenticate users attempting to log in to the system.

15. The system of claim 9, wherein each component server includes scripts that create relational database management system tables to implement a relational data model for that component.

16. The system of claim 9, further comprising a gateway server for interfacing between the object relational server and external software applications supplying source data.

17. The system of claim 9, wherein the components comprise client, problem, encounter, provider and service components to support a healthcare business model.

* * * * *

UNITED STATES PATENT AND TRADEMARK OFFICE
CERTIFICATE OF CORRECTION

PATENT NO. : 6,363,393 B1
DATED : March 26, 2002
INVENTOR(S) : Ribitzky

It is certified that error appears in the above-identified patent and that said Letters Patent is hereby corrected as shown below:

<u>Column 16,</u>
Line 42, replace "da" with -- data --

<u>Column 18,</u>
Line 7, after "component"; insert -- and --

Signed and Sealed this

Seventeenth Day of December, 2002

JAMES E. ROGAN
*Director of the United States Patent and Trademark Office*